United States Patent [19]
Isner et al.

[11] Patent Number: 5,104,393
[45] Date of Patent: * Apr. 14, 1992

[54] CATHETER

[75] Inventors: Jeffrey M. Isner; Richard Clarke, both of Boston, Mass.

[73] Assignee: AngeLase, Inc., Plymouth, Minn.

[*] Notice: The portion of the term of this patent subsequent to Jan. 15, 2008 has been disclaimed.

[21] Appl. No.: 608,281

[22] Filed: Nov. 2, 1990

Related U.S. Application Data

[63] Continuation of Ser. No. 400,701, Aug. 30, 1989, Pat. No. 4,985,028.

[51] Int. Cl.$^5$ .............................................. A61B 17/36
[52] U.S. Cl. ....................................................... 606/15
[58] Field of Search ............... 606/7, 14, 15; 128/397, 128/398

[56] References Cited

U.S. PATENT DOCUMENTS

| | | | |
|---|---|---|---|
| 4,785,815 | 11/1988 | Cohen | 606/7 X |
| 4,854,315 | 8/1989 | Stack et al. | 128/398 X |
| 4,985,028 | 1/1991 | Isner et al. | 606/15 |

FOREIGN PATENT DOCUMENTS 3718139 12/1988 Fed. Rep. of Germany ........ 606/15

OTHER PUBLICATIONS

Isner et al, "Lasers: Their Potential ... ", Cardiovascular Medicine, May 1985, pp. 23-25, 28-30, 37.
Lee et al, "Effects of Laser Radiation ... ", Am. H. J., 1983, pp. 587-590.

*Primary Examiner*—Lee S. Cohen
*Attorney, Agent, or Firm*—Hugh D. Jaeger

[57] ABSTRACT

A technique for the treatment of ventricular tachycardia. The ventricles are endocardially mapped by way of an electrophysiological workup. This mapping locates the tachycardial foci and other abnormalities in conduction. A special catheter containing an optical fiber is percutaneously inserted into a blood vessel and advanced into the ventricle. The distal tip of the catheter is positioned adjacent to each of the tachycardia generating sites. A medical laser is used to irradiate each site via the optical fiber. The tissue at each site is thereby photocoagulated or ablated to remove the source of the tachyarythmia.

1 Claim, 9 Drawing Sheets

CATHETER

This application is a continuation of application Ser. No. 400,701 filed Aug. 30, 1989, now U.S. Pat. No. 4,985,028.

CROSS REFERENCES TO CO-PENDING APPLICATIONS

This application relates to Ser. No. 400,702, filed Aug. 30, 1989, entitled "Catheter" by the same Assignee as this patent application.

BACKGROUND OF THE INVENTION

1. Field of the Invention

The present invention generally relates to treatment of ventricular tachycardia, and more particularly, relates to percutaneous treatment of ventricular tachyarchia using laser energy.

2. Description of the Prior Art

Ventricular tachycardia is a disease of the heart in which the heart's normal rhythmic contraction is altered, thus effecting left ventricular function. The condition is often described as a heart beat which is too fast, although the disease is far more complex. In many patients the orderly contractions of the heart are not present because various portions of the myocardium do not contract and relax in proper synchronism with the rest of the heart.

Currently, the most common treatment for tachycardia is through the use of various drugs. Some drugs reduce the irritability of the offending myocardial tissue, whereas other drugs may slow the response time of all myocardial tissue. In either case the treatment is administered systemically resulting in various side effects.

A second technique now gaining some popularity is surgical intervention. Initially, surgery was performed only in those circumstances which were totally refractory to drug therapy, however, surgical intervention is now more popular. The technique involves electrophysiological mapping of the myocardium. Foci of the tachycardia are located and surgically excised. The major disadvantage of this procedure is the cost and risk associated with open chest cardiac surgery. A description of the surgical procedure may be found in "Endocardial Excision: A new Surgical Technique for the Treatment of Recurrent Ventricular Tachycardia", by Mark E. Josephson, M.D., et al, Circulation, Volume 60, Number 7, 1979.

A first variation on surgical excision involves cryosurgery. In this technique, the diseased myocardial tissue is destroyed by freezing. See for example "The Successful Cryosurgical Treatment of Paroxyal Ventricle Tachycardia", Chest, Volume 75, at page 612, 1979. Other variations involve the use of DC shock and radiofrequency energy.

Perhaps the most promising technique similar to surgical excision is with the use of laser energy. Such a technique is described in "Neodymium: YAG Lase photocoagulation: A Successful New Map-Guided Technique for the Intraoperative Ablation of Ventricular Tachycardia", by Robert H. Svenson, M.D., et al., *Circulation*, Volume 76, Number 6, Dec. 1987. This technique attempts to photocoagulate rather than ablate the diseased tissue. In this way the mechanical integrity of the myocardium is preserved. However, because the method of Svenson, et al. is intraoperative, the major problem with surgical excision (i.e., need to perform a thorocotomy) is not overcome by this technique. The difficulty that remains is the cost and trauma associated with this procedure.

SUMMARY OF THE INVENTION

The present invention alleviates the cost and trauma associated with a thorocotomy. After the myocardium has been mapped and the sites to be treated have been identified, a special catheter is introduced percutaneously and advanced into the left ventricle either transarterially in retrograde fashion, or transceptually after transveneous introduction. The distal tip is positioned adjacent to a site to be treated and maintained in position with fixation means. Energy from a medical laser is supplied to the site via an optical fiber within the special catheter. Upon being irradiated, the myocardial tissue at the identified site is photocoagulated or photoablated. Other sites identified during the mapping process are similarly treated. Because the technique is performed percutaneously without bypass, each ablated or coagulated focus may be immediately tested to ensure that the corresponding tachycardia mode has been successfully treated.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

The present invention is a technique for the percutaneous treatment of tachycardia. This technique involves the electrophysiological mapping of the myocardium to locate foci likely to produce spontaneous depolarization at high rates and other areas of abnormal conduction.

After mapping is complete, a special catheter according to the present invention is introduced into the circulatory system, preferably through a vessel in the leg, and advanced into the heart. The tip of the catheter is maintained in position adjacent to the areas to be treated, and a medical laser transmits energy via an optical fiber in the catheter to photocoagulate and/or photoablate the tissue about each area.

Figure 1:
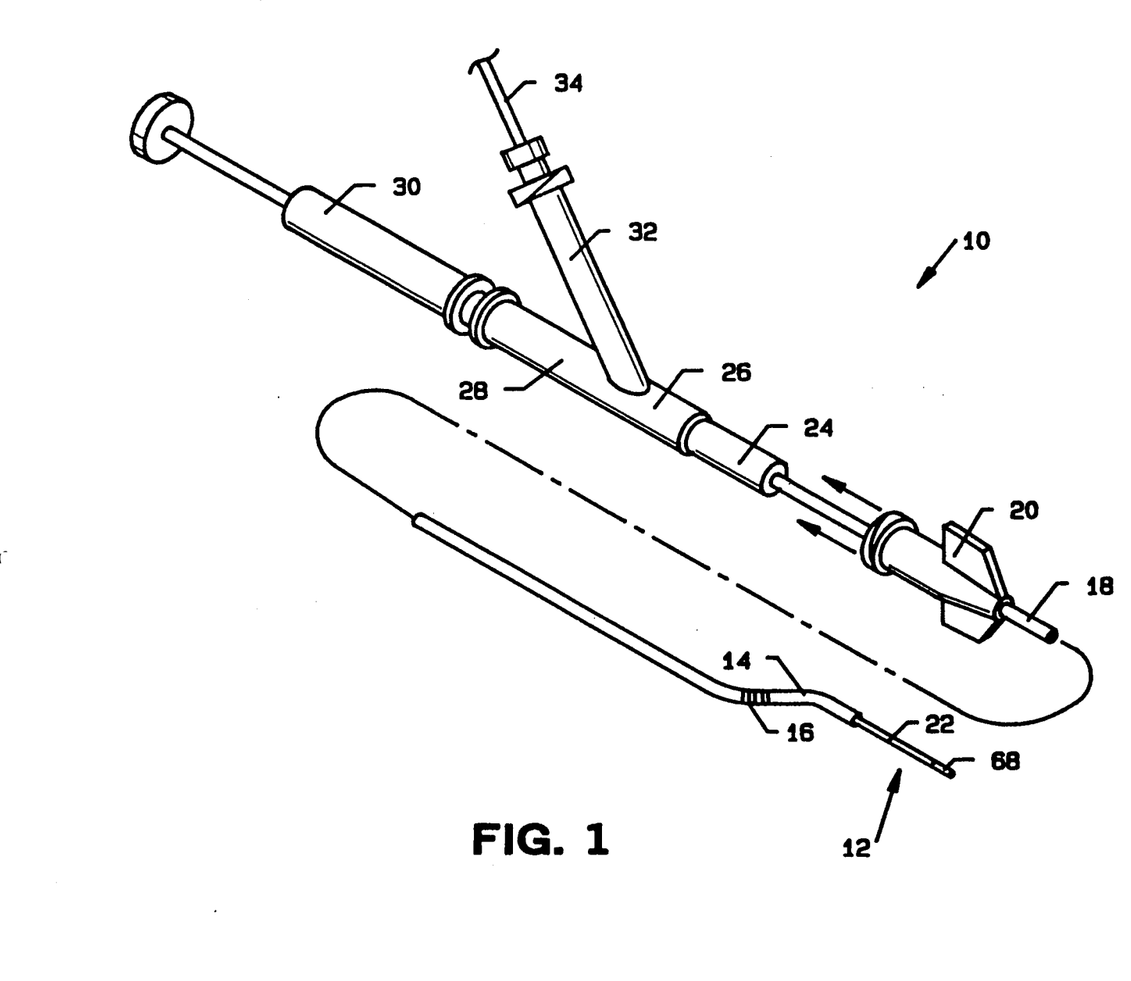
FIG. 1 is a plan view of the catheter of the subject invention.

FIG. 1 is a plan view of catheter 10 of the subject invention. The purpose of catheter 10 is to transmit energy from a medical laser to the myocardium to enable performance of the procedure. This transfer may be transarterial or transveneous as described below. The many aspects of catheter 10 are to optimally facilitate this purpose.

The laser energy is directed to the tissue from distal tip 12. A more detailed view of distal tip 12 is found in FIG. 5. Distal tip 12 is held in position within the ventricle by preformed sigmoidal bend 14 of guiding sheath 18 and fixation wire 42. Distal metal ring 16 provides a radiopaque indication of the location of distal tip 12. For ease of grasping and turning guiding sheath 18, it contains winged member 20 at its proximal end.

The distal end of wye 26 frictionally engages the proximal end of guiding sheath 18 in use, but is shown exploded in FIG. 1 to view the detail. Inner catheter 22 runs the entire length of guiding sheath 18. Inner catheter 22 contains the inner lumen through which runs the optical fiber for transmission of the laser energy and the fixation wire 42. Inner catheter 22 is frictionally coupled via swagging or thermoplasty to metal tubing 24 which runs most of the length of wye 26 and defines the inner lumen of main branch 28 of wye 26. Syringe 30 frictionally engages main branch 28 of wye 26.

Secondary branch 32 of wye 26 receives sheath 34 which contains the optical fiber through which the laser energy is transmitted.

Figure 2:
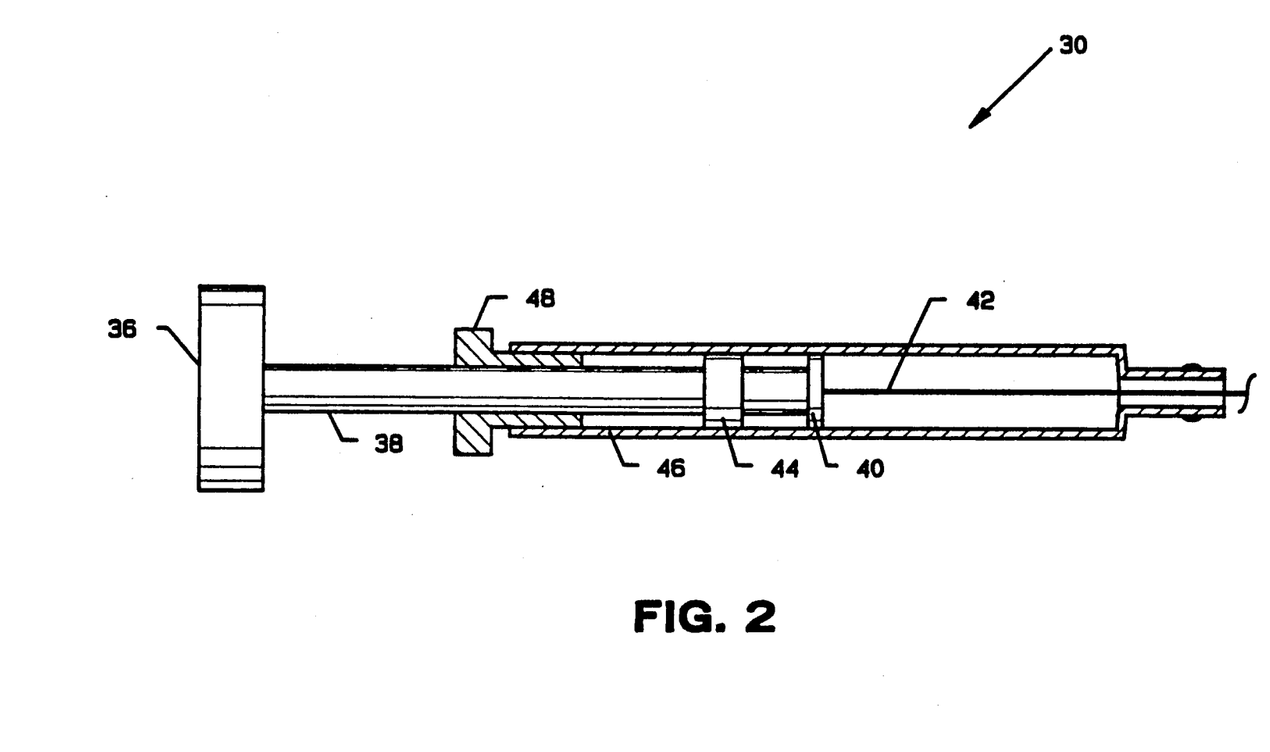
FIG. 2 is a cutaway view of the syringe and the proximal end of the guide wire.

FIG. 2 is a cutaway view of syringe 30. At its most proximal end is thumb knob 36. Depressing thumb knob 36 moves shaft 38 distally which moves piston 40 distally. Fixation wire 42, which runs the entire length of catheter 10, is fixedly attached to piston 40 and is therefore moved distally by pressing thumb knob 36. Fixation wire 42 is substantially stiffer than the inner catheter 22 of catheter 10. The movement of thumb knob 36 (and hence fixation wire 42) in the distal or proximal direction permits medical personnel to fix the position of distal tip 12 of catheter 10 (see also FIG. 1).

Rubber seal 44 sealingly engages wall 46 of syringe 30. Configured stopper 48 guides the movement of shaft 38 for smooth operation. Because syringe 30 is airtight, it may be used for resisting inadvertent proximal or distal movement of fixation wire 42.

Figure 3:
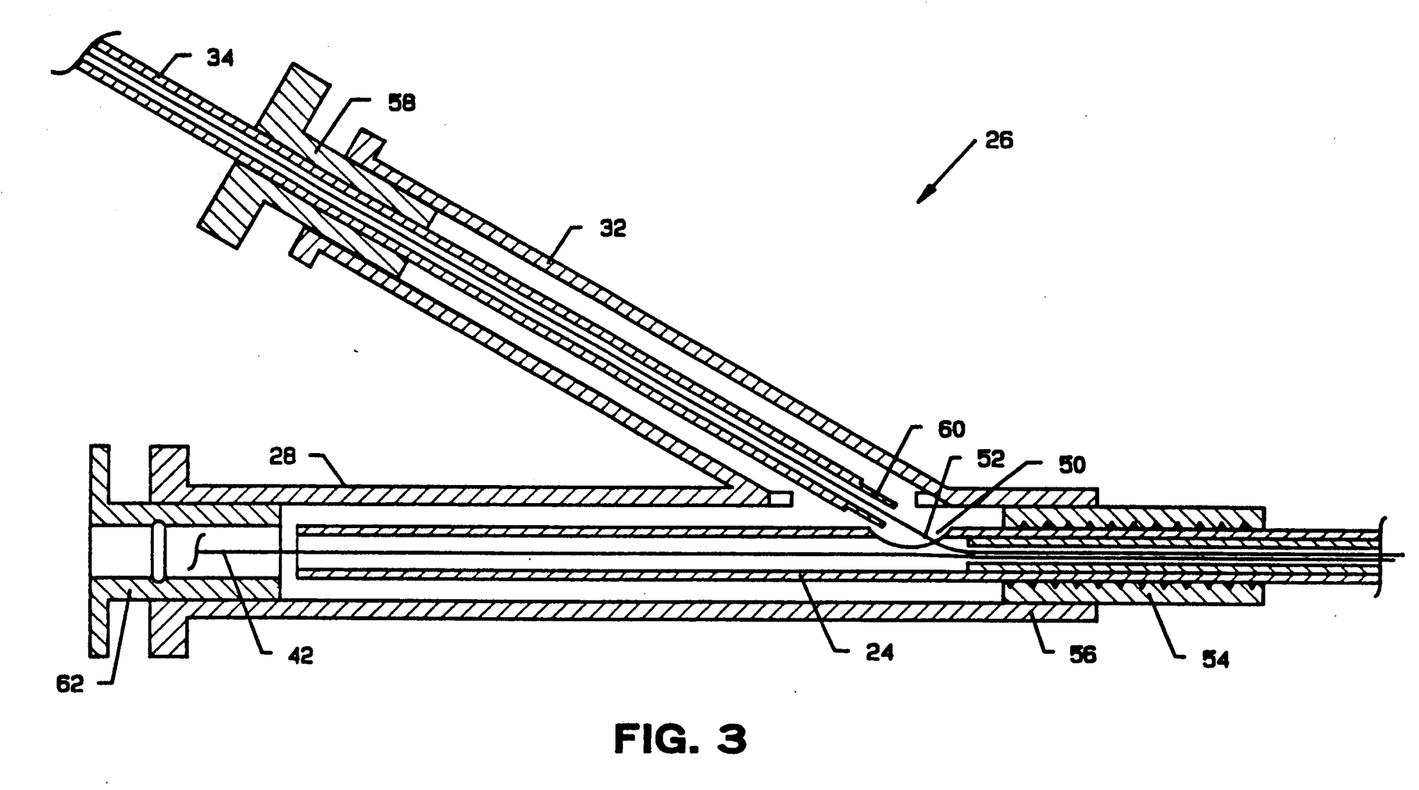
FIG. 3 is a cutaway view of the proximal end of the catheter showing entry of the optical fiber.

FIG. 3 is a cutaway view of wye 26. The outer structure is a molded, rigid plastic. It has a main branch 28 into which syringe 30 is inserted and a secondary branch which receives the optical fiber. As explained above the main branch contains metal tubing 24 which provides a lumen for fixation wire 42. Metal tubing 24 has an aperture 50 which is positioned to receive optical fiber 52. Metal tubing 24 is fixedly engaged by rigid plastic sleeve 54 which in turn is fixedly engaged by the main body of wye 26 and its distal end 56. Rigid plastic sleeve 62 is frictionally engaged by the proximal end of main branch 28. Syringe 30 frictionally engages within the inner diameter of rigid plastic sleeve 62.

Sheath 34 runs the length of secondary branch 32. It provides the lumen for optical fiber 52. Sheath 34 is sealingly engaged by stopper 58 which in turn is sealingly engaged by the proximal end of secondary branch 32. The outer diameter of sheath 34 is decreased at point 60 corresponding to the distal end of secondary branch 32. Sheath 34 terminates at aperture 50 of metal tubing 24.

Figure 4:
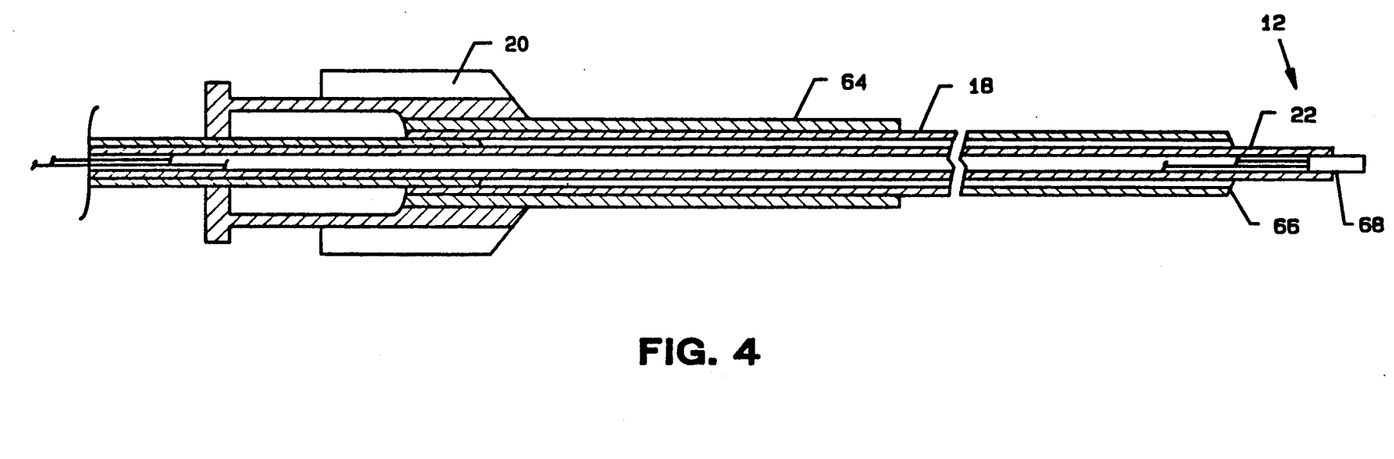
FIG. 4 is a cutaway view of the proximal end of the outer sheath.

FIG. 4 is a cutaway view of the main body of catheter 10. Guiding sheath 18 runs substantially the entire length of catheter 10. Its proximal end is covered by strain relief 64 which is somewhat less flexible than guiding sheath 18, but not rigid. Guiding sheath 18 terminates at point 66 exposing inner catheter 22 which terminates at distal tip 12. Sigmoidal bend 14 and distal metal ring 16 are not shown for clarity, but may be seen in detail in FIG. 5.

Figure 5:
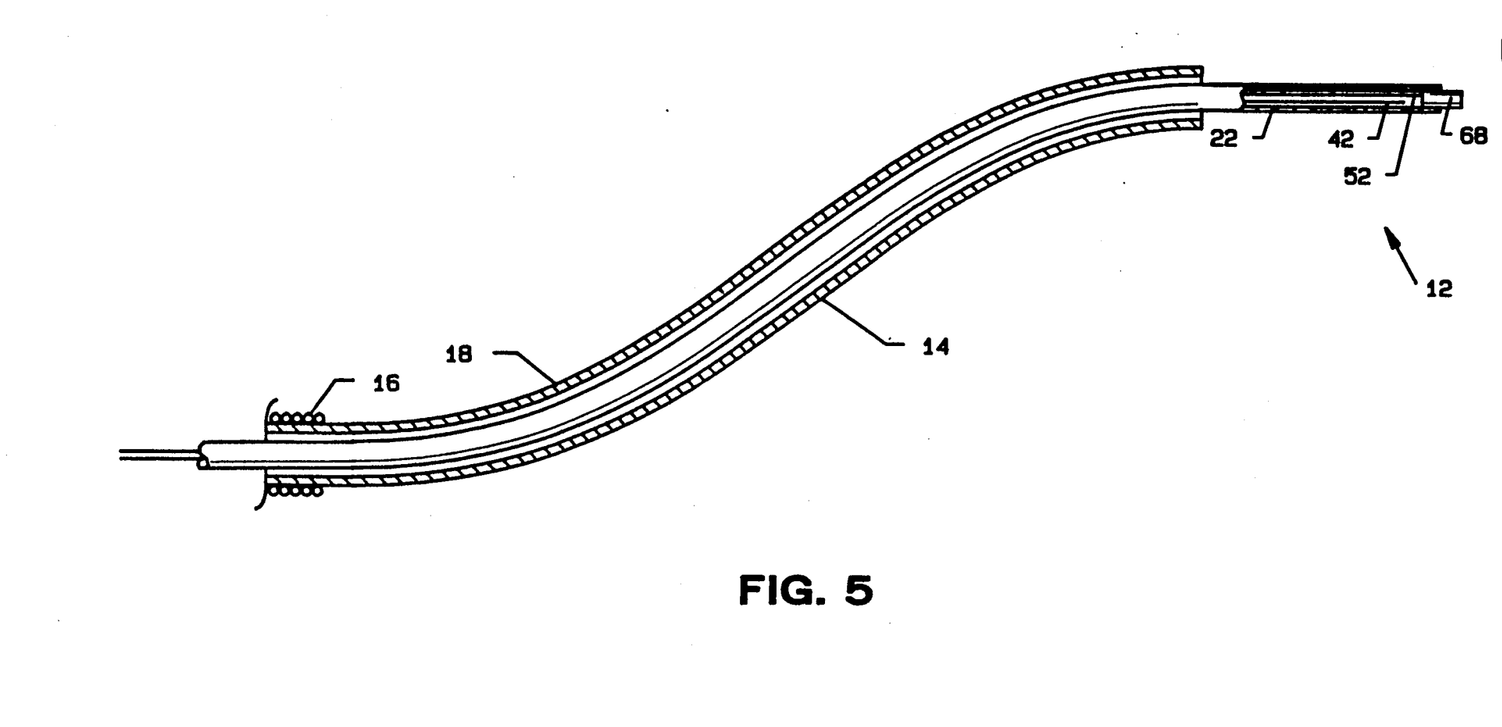
FIG. 5 is a cutaway view of the distal end.

FIG. 5 is a cutaway view of the distal end of catheter 10. Distal tip 12 has a metallic cylinder 68 which frictionally and adhesively engages within inner catheter 22. Metallic cylinder 68 also assists in precisely locating distal tip 12 under fluoroscopy. Optical fiber 52 is fixedly attached within the lumen of metallic cylinder 68 which also aids in energy transfer, in addition to terminating optical fiber 52. Fixation wire 42 terminates just proximal to metallic cylinder 68 when extended maximally in the distal direction. Fixation wire 42 may be advanced and retracted in the manner discussed above to assist in fixation of distal tip 12.

Sigmoidal bend 14 of guiding sheath 18 is preformed. Because guiding sheath 18 is substantially less flexible than inner catheter 22, sigmoidal bend 14 greatly aids in placement of distal tip 12 and in maintaining the desired location. Distal metal ring 16 is placed on sigmoidal bend 14. Because distal metal ring 16 is radiopaque, it is also helpful in identifyinq sigmoidal bend 14 during the procedure.

Figure 6:
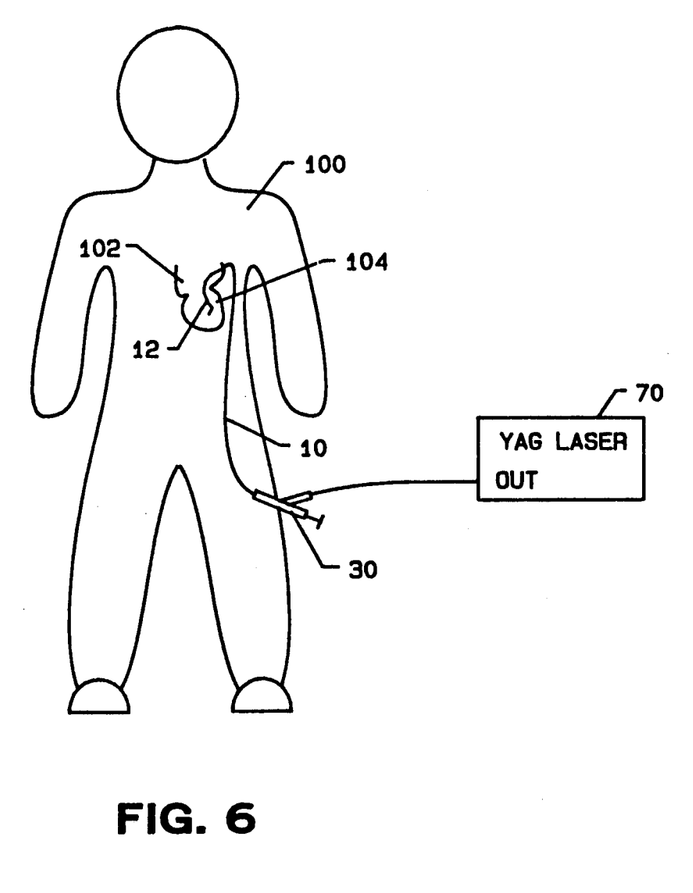
FIG. 6 is a schematic diagram of the procedure using a retrograde femoral approach.

FIG. 6 is a schematic diagram of a percutaneous procedure practicing the present invention. Yag laser 70 is preferably a Model YAG-1 manufactured and sold by Quantronix, Incorporated, although similar products are available elsewhere. Energy from YAG laser 70 is transferred via optical fiber 52 to distal tip 12 placed within left ventricle 104 of heart 102 of patient 100. In this embodiment, catheter 10 is inserted into the femoral artery and proceeds through the aorta into left ventricle 104 via the aortic valve (see also FIG. 7). During operation, the entire catheter system may be cooled by waterflow in the annular space between guiding sheath 18 and inner catheter 22.

Figure 7:
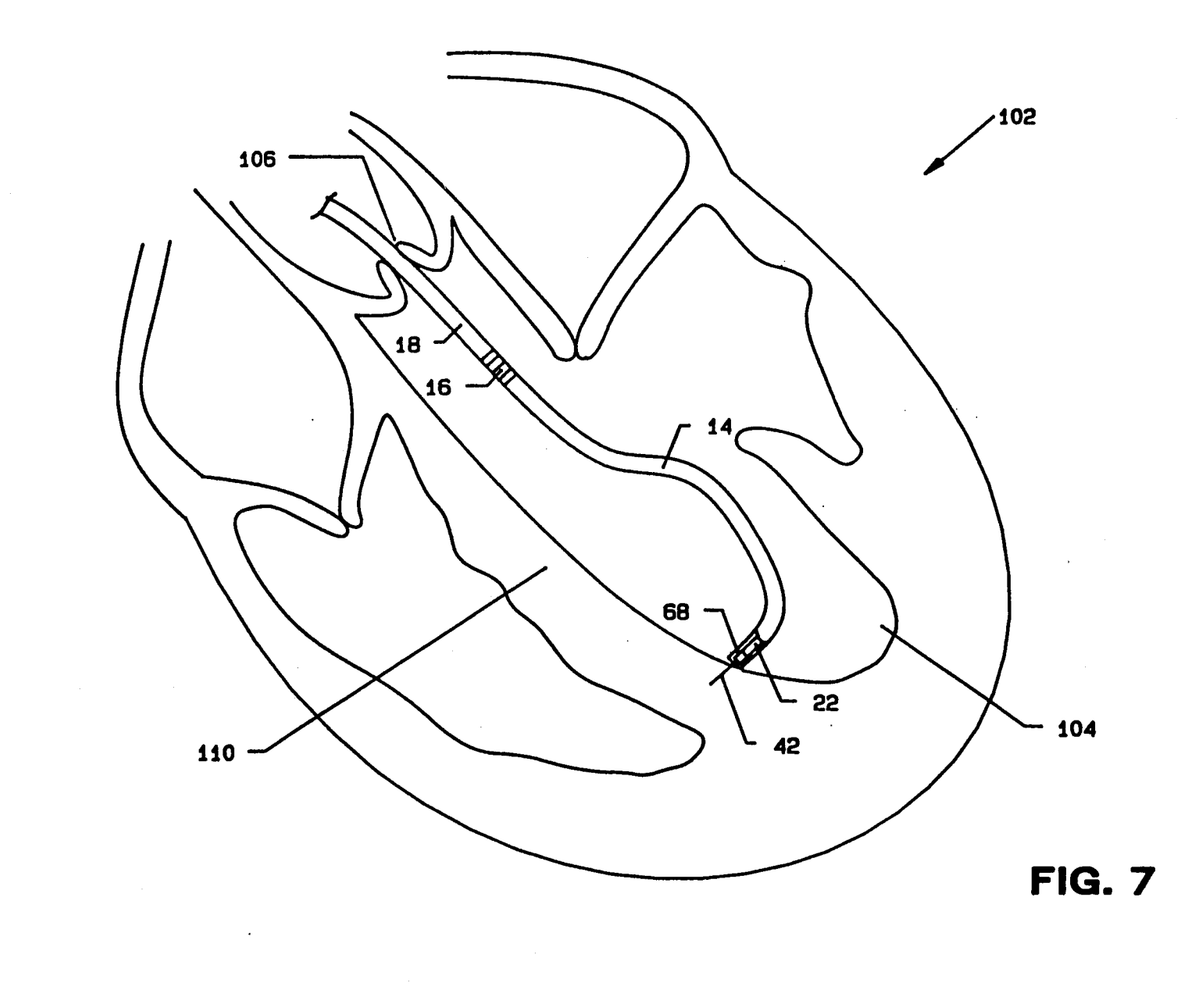
FIG. 7 is a cutaway view of the heart using a retrograde femoral approach.

FIG. 7 shows an enlarged cutaway view of heart 102 undergoing the procedure of the present invention. Heart 102 has been mapped using standard endocardial electrophysiological techniques. The mapping process identifies those areas to be irradiate.

Catheter 10 has been inserted within the femoral artery as shown in FIG. 6 and has been advanced through the aorta into left ventricle 104. Notice sigmoidal bend 14 interacts with the irregular shape within left ventricle 104 to maintain the position of metallic cylinder 68 along the axis of catheter 10. Extension of fixation wire 42 prevents transverse motion. Ideally metallic cylinder 68 is positioned within 1mm of the tissue to be irradiated with the laser energy. Distal metal ring 16 aids in verification of placement using fluoroscopy. Once the exact position of metallic cylinder 68 is fixed by the advancing thumb knob 36 as discussed above.

After correct placement of metallic cylinder 68 is verified, a short burst of laser energy is issued. Preferably the duration is approximately 15 second and the power is approximately 15 watts. This energy is sufficient to either ablate or photocoagulate the tissue associated with the tachycardia foci. Using standard endocardial techniques, the irradiated areas may be immediately tested to ensure that the tachycardia foci have been destroyed.

DESCRIPTION OF THE ALTERNATIVE EMBODIMENT

Figure 8:
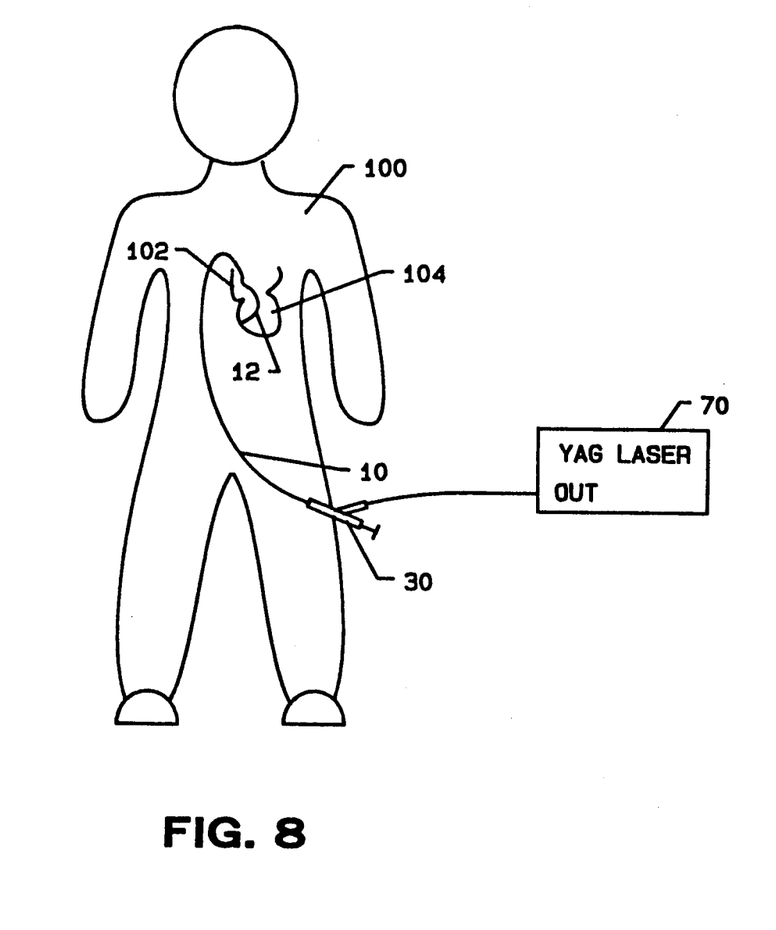
FIG. 8 is a schematic diagram of the procedure using a transceptual approach; and, FIG. 9 is a cutaway view of the heart during ablation using a transceptual approach.

FIG. 8 shows an alternative approach to the procedure. Each of the elements is as shown in FIG. 6. The major exception is that catheter 10 is advanced to heart 102 transveneously. Insertion is preferably made into the femoral vein and is advanced to the right side of heart 102. Left ventricle 104 is entered transeptually as shown in FIG. 9.

Figure 9:
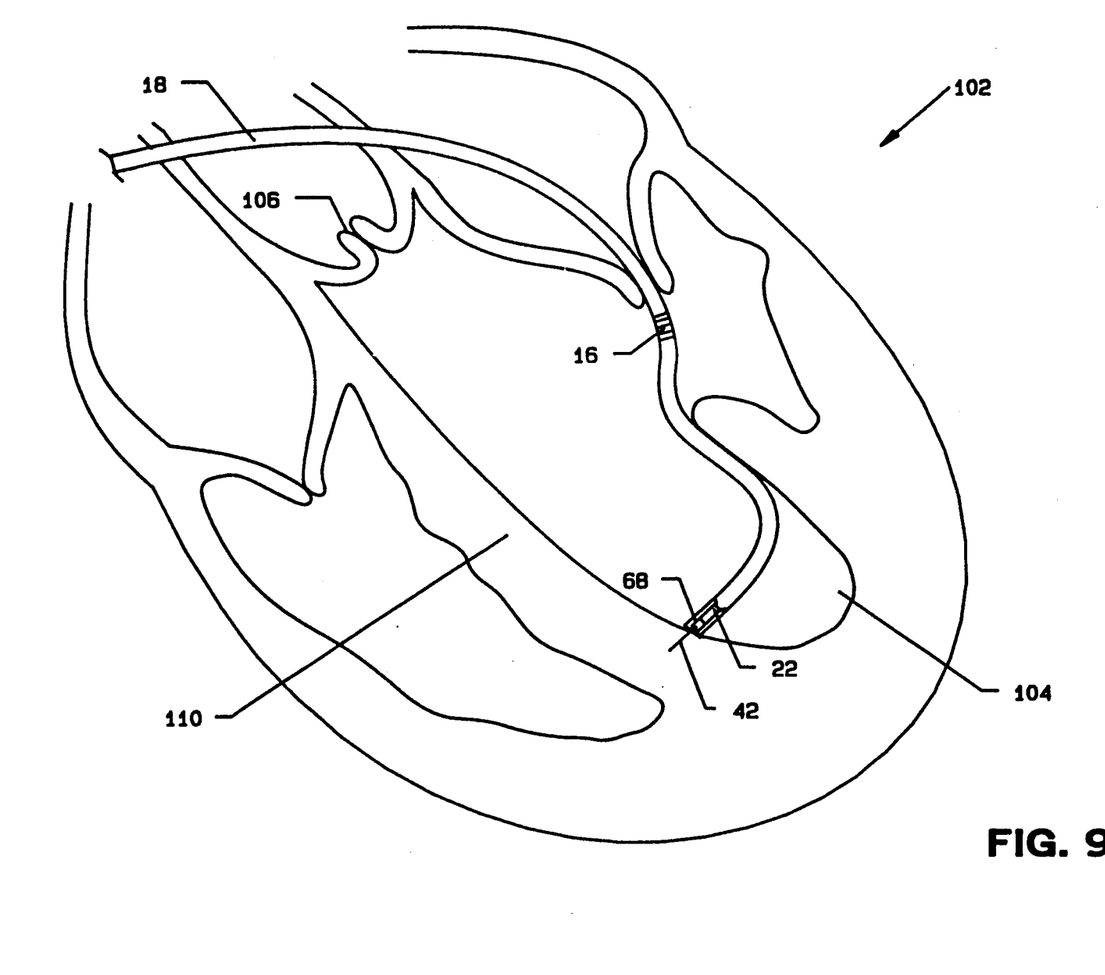

FIG. 9 is a cutaway and enlarged view of heart 102. It differs from FIG. 7 only in that left ventricle 104 is entered transeptually as shown using procedures known in the art.

Having thus described the preferred embodiments of the present invention, those of skill in the art will be able to readily apply these teachings to other embodiments within the scope of the claims hereto appended.

We claim:

1. A process for treating ventricular tachycardia in a patient comprising the steps of:
   a. electrophysiologically mapping a heart of said patient to locate at least one tachycardia focus;
   b. introducing a catheter system into the circulatory system of said patient, said catheter system comprising a lumen through which runs an optical fiber and a single fixation wire;
   c. advancing said catheter system into said heart;
   d. positioning a distal tip of said catheter system adjacent to at least one located tachycardia focus;
   e. fixing said distal tip of said catheter system in place by urging a sigmoidal bend of said catheter system into contact with the inner walls of said heart and by advancing said fixation wire in said catheter system distally so that said fixation wire engages a wall of said heat; and,
   f. irradiating said tachycardia focus with laser energy transmitted by said optical fiber.

* * * * *